(12) United States Patent
Spannagel et al.

(10) Patent No.: US 6,255,603 B1
(45) Date of Patent: Jul. 3, 2001

(54) DRYING SCALE WITH MOVEABLE RADIATING SOURCE AND A METHOD PERFORMED BY THE DRYING SCALE

(75) Inventors: Wilfried Spannagel, Goettingen; August Heine, Bodensee; Norbert Winkler, Noerten-Hardenberg, all of (DE)

(73) Assignee: Shartorious AG, Goettingen (DE)

( * ) Notice: Subject to any disclaimer, the term of this patent is extended or adjusted under 35 U.S.C. 154(b) by 0 days.

(21) Appl. No.: 09/448,833

(22) Filed: Nov. 24, 1999

(30) Foreign Application Priority Data

Nov. 26, 1998 (DE) .............................. 198 54 563

(51) Int. Cl.$^7$ .......................... G01N 25/00; G01N 5/02; G01N 25/56; G01G 21/28
(52) U.S. Cl. ......................... 177/180; 177/238; 177/245; 374/14; 73/76
(58) Field of Search .................................. 374/14; 73/76; 177/245, 180, 238, 239, 240, 241, 242, 243

(56) References Cited

U.S. PATENT DOCUMENTS

| 4,666,007 | 5/1987 | Knothe et al. ........................ 177/245 |
| 4,889,201 | 12/1989 | Oldendorf et al. ................ 177/25.14 |
| 5,064,009 | * 11/1991 | Melcher et al. ...................... 177/245 |
| 5,485,684 | * 1/1996 | Philipp et al. ....................... 177/245 |
| 5,499,532 | * 3/1996 | Kaiho et al. ............................. 73/76 |
| 5,787,600 | 8/1998 | Leisinger et al. ......................... 34/89 |

FOREIGN PATENT DOCUMENTS

| 3305846 | 8/1984 | (DE) . |
| 296 03 227 U | 5/1996 | (DE) . |
| 2278202 | 11/1994 | (GB) . |

\* cited by examiner

Primary Examiner—Randy W. Gibson
(74) Attorney, Agent, or Firm—Sughrue, Mion, Zinn, Macpeak & Seas, PLLC

(57) ABSTRACT

A drying scale is provided that contains a housing, a weighing system, a scale pan, a carriage, and a radiating source. The weighing system is disposed within the housing for weighing a sample, and a scale pan is operably supported by the weighing system and contains the sample to be weighed. The carriage moves between a loading position, and a radiating source is disposed within said carriage. The carriage exposes the scale pan when said carriage is in the loading position and moves the radiating source over at least part of the scale pan such that the radiates heat and dries the sample when the carriage is in the drying position. Also, the weighing system and the scale pan are fixedly disposed with respect to the housing, and the carriage and the radiating source move relative to the housing between the loading position and the drying position. In addition, a method performed by the drying scale is also provided.

35 Claims, 4 Drawing Sheets

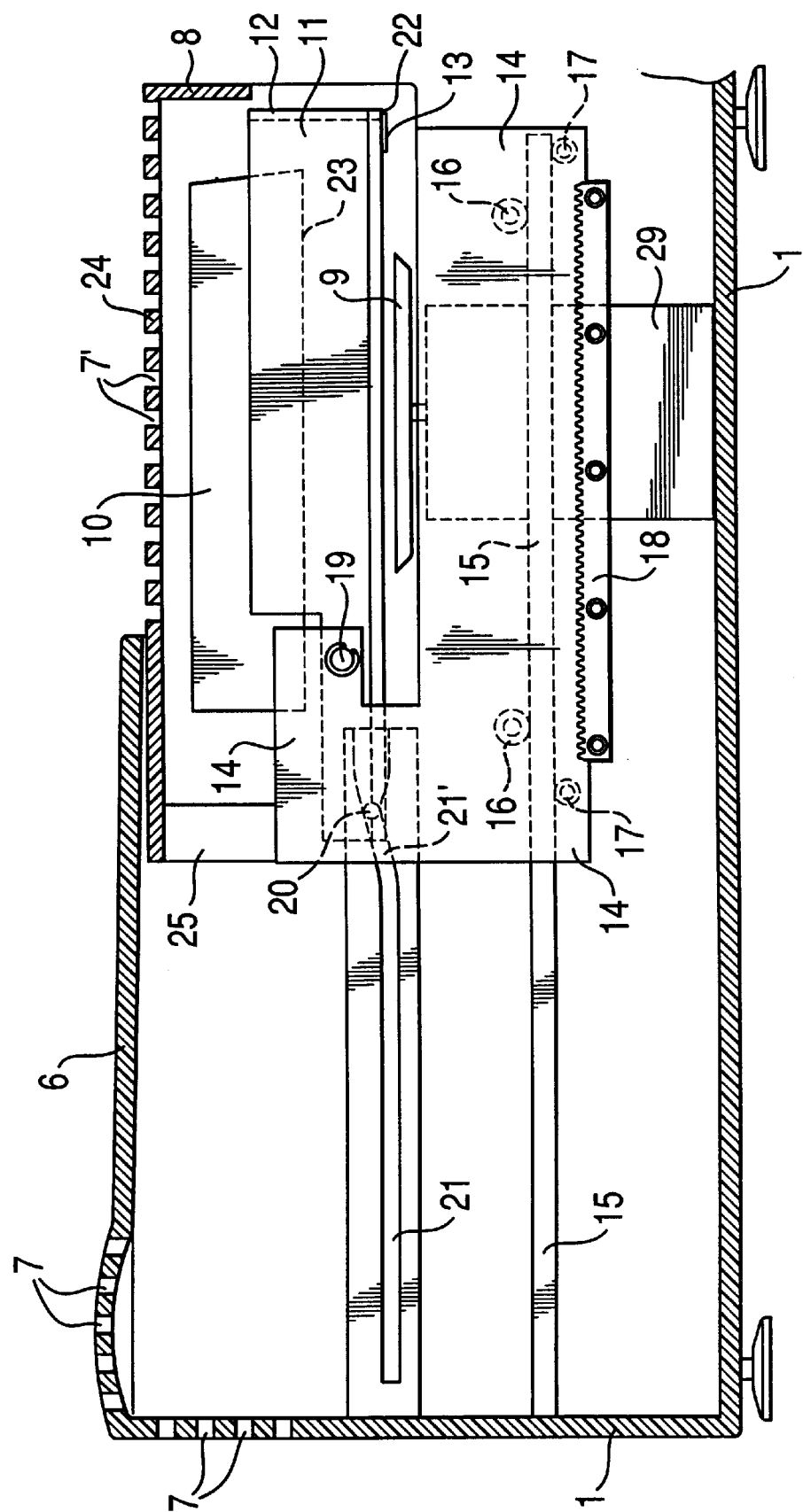

DRYING SCALE WITH MOVEABLE RADIATING SOURCE AND A METHOD PERFORMED BY THE DRYING SCALE

BACKGROUND OF THE INVENTION

1. Field of the Invention

The present invention relates to a drying scale. More particularly, the present invention relates to a drying scale that contains a scale pan that is supported on a weighing system and that has a radiating source for heating and drying weighing material placed on the scale pan. In addition, the present invention relates to a method performed by the drying scale. The following disclosure is based on German Patent Application No. 19854563.0 which was filed on Nov. 26, 1998 and which is incorporated herein by reference.

2. Description of the Related Art

Examples of scales that contain a radiating source for drying samples to be weighed are generally described in U.S. Pat. No. 4,666,007 ("the '007 patent") and U.S. Pat. No. 4,889,201 ("the '201 patent"). Both the '007 patent and the '201 patent are incorporated herein by reference.

As described in the '007 patent, the drying scale is designed such that the radiating source does not obstruct the scale pan when a sample to be weighed is loaded on the scale pan. Specifically, the radiating source is arranged behind the scale pan, and after the sample is loaded onto the pan, a deflecting reflector is unfolded. Then, the thermal radiation produced by the radiation source is reflected via the deflecting reflector onto the scale pan to dry the sample. Afterwards, when the sample is dried, the deflecting reflector is folded away from the sample pan. Although the radiating source is located behind the scale pan so that it does not obstruct the scale pan, a large space exists between the radiating source and the scale pan. Thus, the thermal radiation generated by the source is weakened due to the distance that it must travel to the scale pan and due to reflection losses when it is deflected by the deflecting reflector. Accordingly, the energy efficiency of the drying scale described in the '007 patent is not optimum.

An example of a drying scale that attempts to overcome the above problem is shown in U.S. Pat. No. 5,787,600 ("the '600 patent") which is incorporated herein by reference. As described in the patent, the drying scale contains a scale pan that is located directly below the radiating source when the sample in the pan is being dried. Also, when the sample is to be loaded onto the scale pan, the scale pan is moved out from underneath the radiating source. However, when the scale pan is moved with respect to the radiation source for the purposes of the loading the sample, the weighing system does not move. Thus, a complicated connection, which can be extended and retracted telescopically, between the scale pan and weighing system is required. However, such a complicated connection is extremely susceptible to vertical vibrations and degrades the accuracy of the drying scale.

To attempt to overcome such problem, the '600 patent describes another embodiment in which both the weighing system and scale pan move from underneath the radiating source when a sample is to be loaded into the scale pan. However, such a design does not adequately overcome the above problem because, when the weighing system is moved out from underneath the radiating source, it is very sensitive to vibrations because it extends out from the drying scale. In addition, the various components used to guide the weighing system between the drying position and the loading positing must be extremely precise since the horizontal position of the weighing system must be exactly the same when it is in the drying and loading positions. Therefore, the complexity and cost of the drying scale is substantially increased.

SUMMARY OF THE INVENTION

One object of the present invention to provide a drying scale that has a weighing system that is not very sensitive to external vibrations and that can measure the weight of the sample with significantly increased accuracy.

Another object of the present invention to provide a method performed by a drying scale in which a weighing system of the drying scale is not very sensitive to external vibrations and can measure the weight of the sample with significantly increased accuracy.

A further object of the present invention is to provide a drying scale having relatively low complexity and cost.

A yet further object of the present invention is to provide a method performed by a drying scale having relatively low complexity and cost.

A still further object of the present invention is to provide a drying scale in which the energy efficiency of the drying scale is optimized.

An additional object of the present invention is to provide method performed by a drying scale in which the energy efficiency of the drying scale is optimized.

In order to achieve the above and other objects, a drying scale is provided. The drying scale comprises: a weighing system for weighing a sample; a scale pan that is operably supported by said weighing system and contains the sample to be weighed; and a radiating source that moves between a loading position and a drying position, wherein said radiating source exposes said scale pan when said radiating source is in said loading position and wherein said radiating source covers at least part of said scale pan to radiate heat and dry said sample when said radiating source is in said drying position.

In order to further achieve the above and other objects, a drying scale is provided. The drying scale comprises: a housing; a weighing system disposed within said housing for weighing a sample; a scale pan that is operably supported by said weighing system and contains the sample to be weighed; a carriage that moves between a loading position and a drying position; and a radiating source that is disposed within said carriage, wherein said carriage exposes said scale pan when said carriage is in said loading position, wherein said carriage moves said radiating source over at least part of said scale such that said radiation source radiates heat and dries said sample when said carriage is in said drying position, and wherein said weighing system and said scale pan are fixedly disposed with respect to said housing and said carriage and said radiating source move relative to said housing between said loading position and said drying position.

In order to even further achieve the above and other objects, a method for measuring a sample with a drying scale is provided. The method comprises: (a) placing a sample to be weighed in a scale pan that is operably supported by a weighing system; (b) moving a radiating source to a drying position over at least part of said sample in said scale pan; (c) radiating heat from said radiating source to said sample when said radiating source is in said drying position.

BRIEF DESCRIPTION OF THE DRAWINGS

The above and other objects and advantages of the present invention will become more apparent by describing in detail

FIG. 4 shows a cross-sectional side view of the drying scale in the drying position in accordance with the illustrative embodiment of the present invention.

DETAILED DESCRIPTION OF THE PREFERRED EMBODIMENTS

The following description of the preferred embodiments discloses specific configurations and components. However, the preferred embodiments are merely examples of the present invention, and thus, the specific features described below are merely used to more easily describe such embodiments and to provide an overall understanding of the present invention. Accordingly, one skilled in the art will readily recognize that the present invention is not limited to the specific embodiments described below. Furthermore, the descriptions of various configurations and components of the present invention that would have been known to one skilled in the art are omitted for the sake of clarity and brevity.

Figure 1:
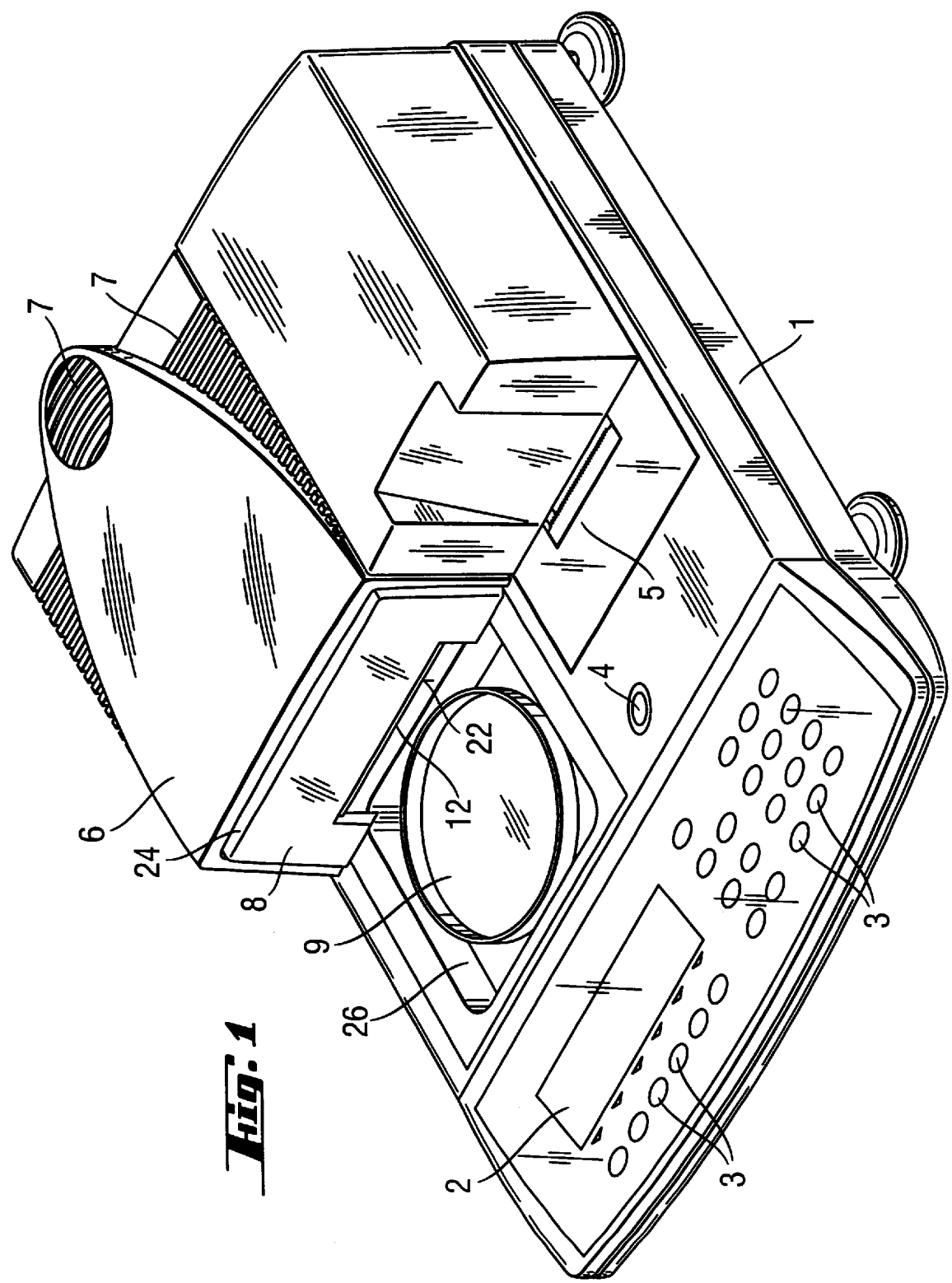
FIG. 1 shows a perspective view of a drying scale in a loading position in accordance with an illustrative embodiment of the present invention.
Figure 2:
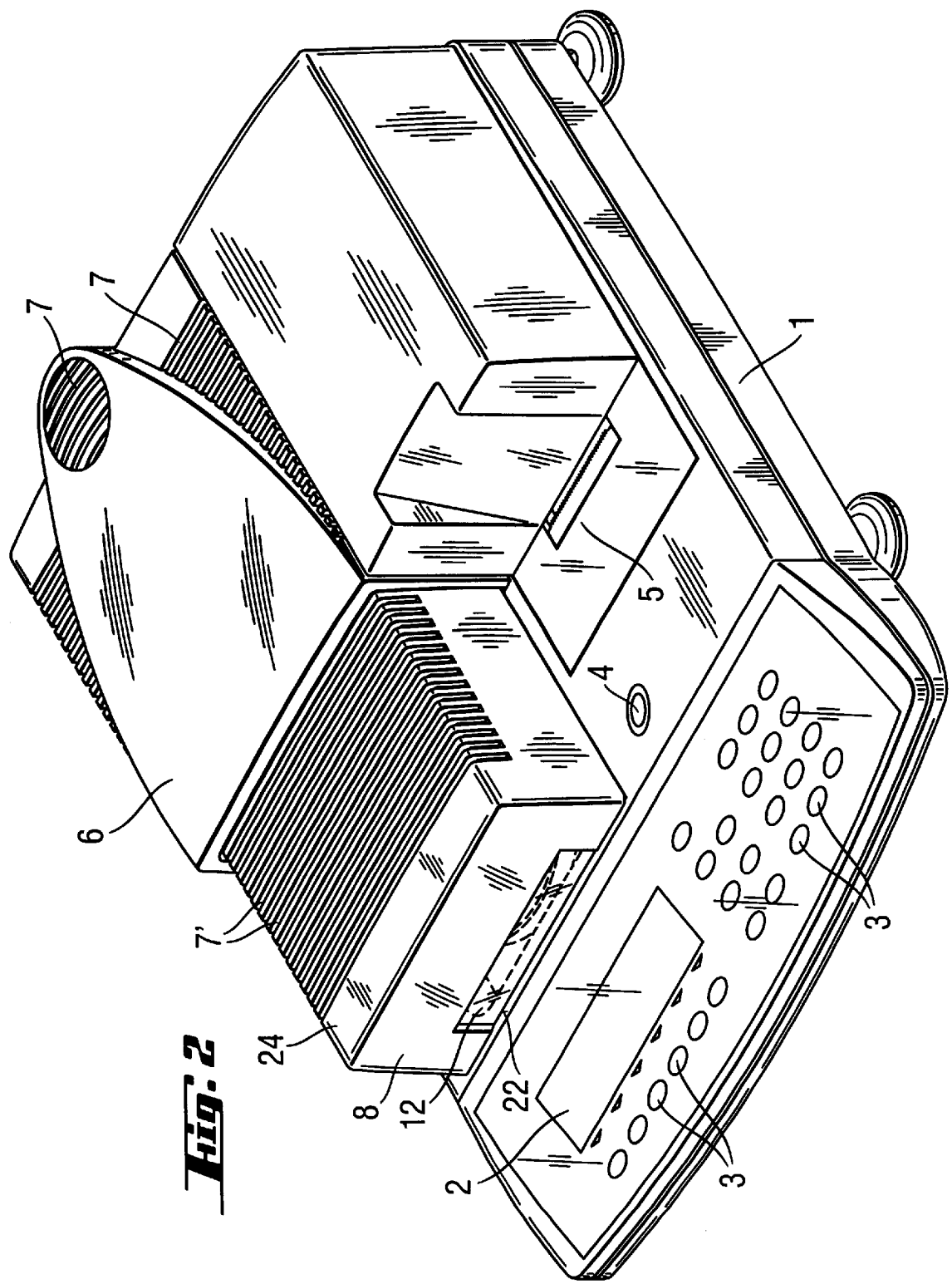
FIG. 2 shows a perspective view of the drying scale in a drying position in accordance with the illustrative embodiment of the present invention.

FIG. 1 is a perspective view of the drying scale in a loading position in accordance with an illustrative embodiment of the present invention, and FIG. 2 is a perspective view of the drying scale in a drying position in accordance with the illustrative embodiment. As shown in the figures, the drying scale comprises a housing 1, a display 2, operating keys 3, an air level 4, a printer 5, a covering housing 6, and ventilation openings 7. Upon reading the specification, one skilled in the art will readily know the operations and functions of the display 2, operating keys 3, air level 4, and printer 5, and thus, such components are not described in extensive detail.

As further shown in FIG. 1, the drying scale contains a scale pan 9 which is exposed when the scale is in a loading position. In the loading position, an operator can measure a sample to be weighed, place it in the scale pan 9, and monitor the display 2 to ensure that the proper amount of the sample is placed in the pan 9. The scale pan 9 is located in a recessed portion of the housing 1 to protect the sample from drafts, and the walls of the recessed portion are lined with a sheet metal or plastic part 26 that can be removed for cleaning.

A radiating source 10 that provides thermal radiation for drying the sample is hidden below the covering housing 6 within a carriage 14. The carriage contains (or is connected to) a carriage cover 24 and a front cover 8. The carriage cover 24 contains ventilation openings 7' and covers the top and sides of the radiating source 10 to prevent the operator of the scale from accidentally contacting the radiating source 10 and becoming burned. The carriage 14 can be moved horizontally between the loading position (FIGS. 1 and 3) and a drying position (FIGS. 2 and 4). When the carriage 14 is in the loading position, the carriage 14 and the radiating source 10 are retracted underneath the covering housing 6 to expose the scale pan 9, and the operator can easily place a sample into the pan 9. On the other hand, when the carriage 14 is moved to the drying position, the carriage 14 and radiating source 10 are placed over the scale pan 9, and the radiation source 10 applies thermal radiation to the sample to dry it. Furthermore, when the carriage 14 and radiating source 10 are moved between the loading position and the drying position, the scale pan 9 and a weighing system 29 located below the pan 9 remain fixed with respect to the housing 1 and are not displaced.

Figure 3:
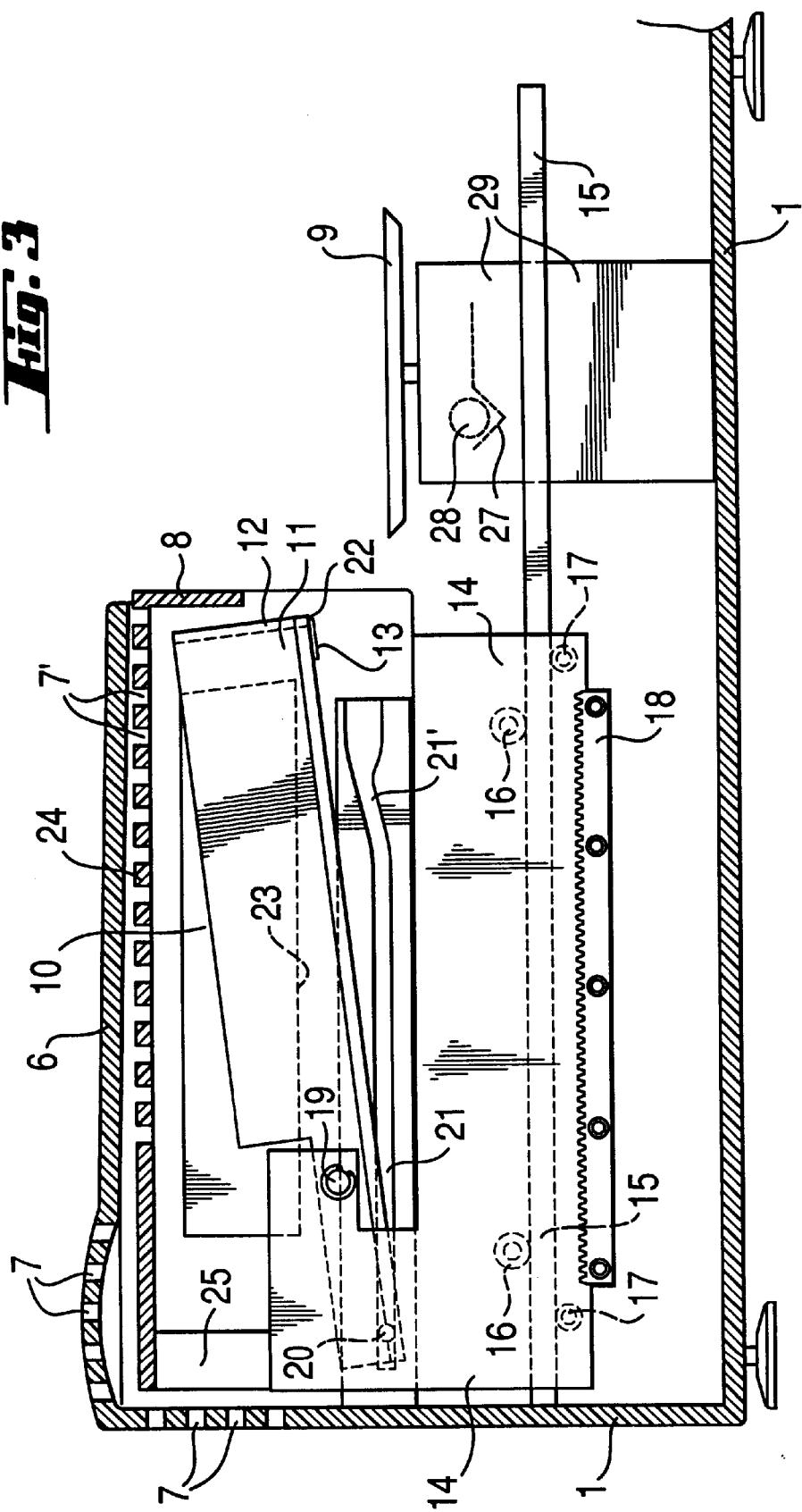
FIG. 3 shows a cross-sectional side view of the drying scale in the loading position in accordance with the illustrative embodiment of the present invention.

Also, as shown in FIGS. 3 and 4, the carriage cover 24 and the front cover 8 are fastened together by lateral plates 25 and other connections that are not shown on the carriage 14. Thus, the carriage cover 24 and front cover 8 both move together with the carriage 14. In addition, most of the carriage cover 24 disappears below the covering housing 6 when the carriage 14 is moved to the loading position. (FIGS. 1 and 3). On the other hand, when the carriage 14 is moved to the drying position, the carriage cover 24 extends far from beneath the covering housing 6. (FIGS. 2 and 4).

As best shown in FIGS. 2 to 4, a viewing window 12 is located within the carriage cover 24 between the front cover 8 and the radiating source 10. When the carriage 14 and radiating source 10 are in the drying position, a lower edge 22 of the viewing window 12 is placed on the top side of the housing 1, and thus, the front portion of the scale pan 9 is sealed. Nonetheless, the sample within the scale pan 9 can be observed and monitored by the operator through the window 12. On the other hand, as the carriage 14 and radiating source 10 are retracted from the drying position to the loading position shown in FIG. 1, the viewing window 12 is raised. As will be described in more detail below, the viewing window 12 quickly raises soon after the carriage 14 begins to retract from the drying position (FIG. 2) and remains raised as the carriage 14 fully retracts to the loading position (FIG. 1). Conversely, when the carriage 14 is moved from the loading position (FIG. 1) to the drying position (FIG. 2), the window 12 is not lowered until shortly before reaching the drying position. By raising and lowering the viewing window 12 in the above manner, the window 12 is prevented from contacting the upper portion of the sample on the scale pan 9 when the carriage 14 is retracted from the drying position to the loading position (or moved to the drying position from the loading position). As a result, the amount of the sample in the pan 9 is not disturbed, the measurement of the weight of the sample is more accurate, and the possibility that the sample becomes contaminated is decreased.

FIGS. 3 and 4 are cross-sectional side views of the illustrative embodiment of the present invention and show the structure of various components of the drying scale in more detail. Specifically, FIG. 3 shows the drying scale when the carriage 14 is in the loading position, and FIG. 4 shows the drying scale when the carriage 14 is in the drying position.

As indicated in the figures, the carriage 14 is supported within the housing 1 by two guide rails 15 that are fixed with respect to the housing 1. Upper rollers 16 are rotatably connected to the carriage 14 and are disposed above the guide rails 15, and lower rollers 17 are rotatably connected to the carriage 14 and are disposed below the guide rails 15. Furthermore, although only one of the two guide rails 15 can be seen in FIGS. 3 and 4, the second guide rail 15 is disposed on the opposite side of the carriage 14 and supports the carriage 14 via upper and lower rollers 16 and 17 in a similar manner.

The carriage 14 is driven horizontally between the loading position and the drying position by a motor (not shown). The motor (not shown) is fixed with respect to the housing 1 and has a pinion (not shown) which engages two racks 18 that are secured to each side of the carriage 14. In FIGS. 3 and 4, only one of the racks 18 is shown for the sake of clarity. As the motor (not shown) rotates, the pinion (not shown) engages the racks 18 and moves them laterally, and the carriage 14 moves laterally in response to the movement of the racks 18. In addition, stoppers and end switches (not shown) are preferably provided in the drying scale to limit the lateral mobility of the carriage 14.

As described above, the radiating source 10 is fastened on the carriage 14 such that it moves when the carriage 14 moves. In addition, the viewing window 12 is connected to the carriage 14 via two axles 19 and two levers 11. As shown in FIGS. 3 and 4, the first axle 19 is connected to one side of the carriage 14, and the first lever 11 is pivotably supported by the first axle 19. Although not shown, the second lever 11 is connected to the opposite side of the carriage 14 via the second axle 19 in a similar manner. Furthermore, the window 12 is connected to the front edges of the two levers 11 such that the window 12 is pivotably supported by the first and second axles 19.

The relative orientation between the levers 11 and the carriage 14 is determined based on the positions of first and second pins 20 within first and second guide grooves 21 disposed within the housing 1. As shown in the figures, one end of the first pin 20 is connected to the first lever 11, and the second end of the first pin 20 is disposed within the first guide groove 21. Although not shown in the figures, the second lever 11, second pin 20, and second guide groove 21 are interconnected in a similar manner. As illustrated in FIG. 3, when the carriage 14 is in the loading position, the pins 20 are located in a rear portion of the guide grooves 21. Accordingly, the levers 11 are pivoted around the axles 19 such that the viewing window 12 is raised to cover a front portion of the radiating source 10.

Then, as the carriage 14 is moved towards the drying position shown in FIG. 4, the pins 20 travel forward through the guide grooves 21. When the pins 20 travel through an initial portion of the grooves 21, the levers 11 remain in a position such that the window 12 remains raised and continues to cover the front portion of the radiating source 10. However, as the pins 20 travel further in the guide grooves 21 and almost reach the end of the grooves 21, the pins 20 travel up oblique sections 21' within the guide grooves 21. As a result, the levers 11 are rotated clockwise around the axles 19, and the viewing window 12 is lowered such that a buffer 13 located beneath the front edge 22 of the window 12 contacts the housing 1 (See FIGS. 2 and 4). (The portion of the housing 1 that contacts the buffer 3 is not shown in FIG. 4 for the sake of clarity). Based on the above configuration, the viewing window 12 is not lowered from its raised position to contact the housing 1 until it has passed over the scale pan 9. Accordingly, the possibility that the window 12 will contact a sample placed in the scale pan 9 when the carriage 14 is moved to the drying position is extremely small.

The difference between the heights of the oblique sections 21' of the guide grooves 21 and the remaining portions of the guide groove 21 is selected such that the viewing window 12 is raised sufficiently so that its lower edge 22 is located just below a lower edge 23 of the radiating source 10 (FIG. 3). With such a design, the viewing window 12 will not contact the sample when the carriage 14 moves back and forth between the loading position and drying position as long as the height of the sample within the scale pan 9 is less than or equal to a maximum permitted height.

However, if the operator fills the scale pan 9 with the sample such that the height is greater than the maximum height, the portion of the sample that extends above the maximum height will be pushed away by the lower edge 22 of the viewing window 12 when the carriage 14 moves to the drying position. In such a situation, a portion of the sample may adhere to the viewing window 12 and may possibly be pushed out of the scale pan 9. Nonetheless, such operation prevents the more severe problem of the sample contacting the hot radiating source 10, adhering to the source 10, and possibly becoming carbonized.

As best shown in FIG. 3, the drying scale comprises a weighing system 29 that is disposed below the scale pan 9. FIG. 4 illustrates the weighing system 29, although it is partially hidden behind the carriage 14. The weighing system 29 is fixedly disposed relative to the housing 1, and thus, even when vibrations occur, the weighing system 29 does not vibrate with respect to the housing 1.

In order to check and, if appropriate, readjust the sensitivity of the drying scale, a calibration weight, which is operably connected to the measuring sensor of the scale by motor or by hand, is typically installed. Such a calibration weight is preferably incorporated into the drying scale of the present embodiment. As shown in FIG. 3, a calibration weight 28 and the associated actuating mechanism 27 are incorporated into the weighing system 29. However, for the sake of clarity, they are not illustrated in FIG. 4. The configuration and operation of the actuating mechanism 27, calibration weight 28, and weighing system 29 will be readily known to one skilled in the art upon reading the specification, and thus, such description is omitted for the sake of brevity.

As described above in accordance with the illustrative embodiment of the present invention, a sample is loaded into the scale pan 9 by moving the radiating source 10 to a loading position. Afterwards, when the sample is to be dried, the radiating source 10 is moved from the loading position to a drying position over the sample. In other words, the scale pan 9 and weighing system 29 do not move with respect to the housing 1 when the radiating source moves between the loading and drying positions. As a result, the weighing system 29 it not very sensitive to external vibrations and can measure the weight of the sample with significantly increased accuracy. In addition, since the scale pan 9 and weighing system 29 are fixedly disposed with respect to the housing 1, complicated components for precisely guiding the weighing system between a drying position and a loading positing are unnecessary. Thus, the complexity and cost of the drying scale is relatively low.

As further described above, the radiating source 10 is moved directly over the sample within the scale pan 9 when the sample is to be dried. Thus, the thermal radiation generated by the radiation source 10 does not need to travel a significant distance or be deflected to reach the sample. Accordingly, the energy efficiency of the drying scale is optimized.

The previous description of the preferred embodiments is provided to enable a person skilled in the art to make and use the present invention. Moreover, various modifications to these embodiments will be readily apparent to those skilled in the art, and the generic principles and specific examples defined herein may be applied to other embodiments without the use of inventive faculty. For example, the specific components and configurations used to move the radiation source 10 between the loading position and the drying position and to raise and lower the viewing window 12 are clearly not limited to the components illustrated in the figures. Furthermore, one skilled in the art will readily recognize, upon reading the present application, that many different types of configurations can be used to move the radiation source 10 and window 12. Therefore, the present invention is not intended to be limited to the embodiments described herein but is to be accorded the widest scope as defined by the limitations of the claims and equivalents thereof.

What is claimed is:

1. A drying scale comprising:
   a weighing system for weighing a sample;
   a scale pan that is operably supported by said weighing system for containing said sample to be weighed; and
   a radiating source that moves between a loading position and a drying position, wherein said radiating source exposes said scale pan when said radiating source is in said loading position and wherein said radiating source covers at least part of said scale pan to radiate heat and dry said sample when said radiating source is in said drying position.

2. The drying scale as claimed in claim 1, further comprising:
   a housing,
   wherein said weighing system and said scale pan are fixedly disposed with respect to said housing and said radiating source moves relative to said housing between said loading position and said drying position.

3. The drying scale as claimed in claim 1, further comprising:
   a carriage that at least partially surrounds said radiating source and moves said radiating source to said loading position and said drying position.

4. The drying scale as claimed in claim 3, wherein said carriage comprises a carriage cover that covers a upper side of said radiating source.

5. The drying scale as claimed in claim 4, wherein said carriage cover covers lateral sides of said radiating source.

6. The drying scale as claimed in claim 3, wherein said carriage comprises a front cover that covers a front portion of said radiating source.

7. The drying scale as claimed in claim 6, wherein said front cover passes completely over said sample when said carriage moves to said drying position, and
   wherein said front cover contains a viewing notch in a bottom edge of said front cover so that an operator of said drying scale can view said sample through said front cover when said carriage is located in said drying position.

8. The drying scale as claimed in claim 7, further comprising:
   a viewing window that is operably connected to said carriage and moves between said loading position and said drying position with said carriage,
   wherein said viewing window is lowered adjacent to said viewing notch when said carriage is moved to said drying position so that said sample is not substantially exposed via said viewing notch, and
   wherein said viewing window is raised with respect to said front cover when said carriage is moved from said drying position to said loading position.

9. The drying scale as claimed in claim 8, wherein at least a portion of said viewing notch of said front cover is located below a lower edge of said radiating source, and
   wherein said viewing window is raised such that a lower edge of said viewing window is located just below said lower edge of radiating source when said carriage is moved from said drying position to said loading position.

10. The drying scale as claimed in claim 8, further comprising:
    a first lever pivotably mounted with respect to said carriage,
    wherein said viewing window is operably connected to said first lever,
    wherein said first lever pivots with respect to said carriage as said carriage moves from said drying position to said loading position to raise said viewing window and pivots with respect to said carriage as said carriage moves from said loading position to said drying position to lower said viewing window.

11. The drying scale as claimed in claim 10, further comprising:
    a first pin operably connected to said first lever; and
    a first guide groove, wherein said first pin slides within said first guide groove as said carriage moves between said drying position and said loading position, and
    wherein said first lever pivots in accordance with a position of said first pin within said first guide groove.

12. The drying scale as claimed in claim 10, further comprising:
    a second lever pivotably mounted with respect to said carriage,
    wherein said viewing window is operably connected to said second lever,
    wherein said second lever pivots with respect to said carriage as said carriage moves from said drying position to said loading position to raise said viewing window and pivots with respect to said carriage as said carriage moves from said loading position to said drying position to lower said viewing window, and
    wherein said first lever and said second lever are disposed on opposite sides of said radiating source.

13. The drying scale as claimed in claim 12, further comprising:
    a first pin operably connected to said first lever;
    a second pin operably connected to said second lever;
    a first guide groove, wherein said first pin slides within said first guide groove as said carriage moves between said drying position and said loading position; and
    a second guide groove, wherein said second pin slides within said second guide groove as said carriage moves between said drying position and said loading position,
    wherein said first lever pivots in accordance with a position of said first pin within said first guide groove, and
    wherein said second lever pivots in accordance with a position of said second pin within said second guide groove.

14. The drying scale as claimed in claim 3, further comprising:
    a rack that is fixedly coupled with respect to said carriage;
    a pinion that engages said rack; and
    a motor that drives said pinion such that said pinion moves said carriage between said loading position and said drying position via said rack.

15. The drying scale as claimed in claim 1, wherein said weighing system comprises:
    a calibration weight circuit that activates a weight motor for operably connecting a calibration weight to the weighing system.

16. A drying scale comprising:

a housing;

a weighing system disposed within said housing for weighing a sample;

a scale pan that is operably supported by said weighing system for containing said sample to be weighed;

a carriage that moves between a loading position and a drying position; and a radiating source that is connected to and moves in accordance with said carriage, wherein said radiating source said scale pan when said carriage is in said loading position, wherein said carriage moves said radiating source over at least part of said scale pan such that said radiation source radiates heat and dries said sample when said carriage is in said drying position, and wherein said weighing system and said scale pan are fixedly disposed with respect to said housing and said carriage and said radiating source move relative to said housing between said loading position and said drying position.

17. The drying scale as claimed in claim 16, wherein said carriage comprises a front cover that covers a front portion of said radiating source, wherein said front cover passes completely over said sample when said carriage moves to said drying position, and wherein said front cover contains a viewing notch in a bottom edge of said front cover so that an operator of said drying scale can view said sample through said front cover when said carriage is located in said drying position.

18. The drying scale as claimed in claim 17, further comprising:

a viewing window that is operably connected to said carriage and moves between said loading position and said drying position with said carriage, wherein said viewing window is lowered adjacent to said viewing notch when said carriage is moved to said drying position so that said sample is not substantially exposed via said viewing notch, and wherein said viewing window is raised with respect to said front cover when said carriage is moved from said drying position to said loading position.

19. The drying scale as claimed in claim 18, wherein at least a portion of said viewing notch of said front cover is located below a lower edge of said radiating source, and wherein said viewing window is raised such that a lower edge of said viewing window is located just below said lower edge of radiating source when said carriage is moved from said drying position to said loading position.

20. The drying scale as claimed in claim 19, further comprising:

a first lever pivotably mounted with respect to said carriage; and a second lever pivotably mounted with respect to said carriage, wherein said viewing window is operably connected to said first lever and said second lever and wherein said first lever and said second lever are disposed on opposite sides of said radiating source, and wherein said first lever and said second lever pivot with respect to said carriage as said carriage moves from said drying position to said loading position to raise said viewing window and pivot with respect to said carriage as said carriage moves from said loading position to said drying position to lower said window.

21. The drying scale as claimed in claim 20, further comprising:

a first pin operably connected to said first lever;

a second pin operably connected to said second lever;

a first guide groove, wherein said first pin slides within said first guide groove as said carriage moves between said drying position and said loading position; and a second guide groove, wherein said second pin slides within said second guide groove as said carriage moves between said drying position and said loading position, wherein said first lever pivots in accordance with a position of said first pin within said first guide groove, and wherein said second lever pivots in accordance with a position of said second pin within said second guide groove.

22. The drying scale as claimed in claim 21, further comprising:

a rack that is fixedly coupled with respect to said carriage;

a pinion that engages said rack; and a motor that drives said pinion such that said pinion moves said carriage between said loading position and said drying position via said rack.

23. The drying scale as claimed in claim 17, further comprising:

a rack that is fixedly coupled with respect to said carriage;

a pinion that engages said rack; and a motor that drives said pinion such that said pinion moves said carriage between said loading position and said drying position via said rack.

24. The drying scale as claimed in claim 22, wherein said carriage comprises a carriage cover that covers a upper side and two lateral sides of said radiating source.

25. A method for measuring a sample with a drying scale, comprising:

(a) placing a sample to be weighed in a scale pan that is operably supported by a weighing system;

(b) moving a radiating source to a drying position over at least part of said sample in said scale pan; and (c) radiating heat from said radiating source to said sample when said radiating source is in said drying position.

26. The method as claimed in claim 25, further comprising:

(d) moving said radiating source from said drying position to a loading position away from said sample in said scale pan such that said radiating source exposes said sample in said scale pan when said radiating source is in said loading position.

27. The method as claimed in claim 25, wherein said step (a) comprises:

(a1) moving said radiating source from said drying position to a loading position such that said radiating source exposes said scale pan when said radiating source is in said loading position; and (a2) placing said sample to be weighed in said scale pan when said radiating source is in said loading position.

28. The method as claimed in claim 27, wherein said weighing system and said scale pan are fixedly disposed with respect to a housing of said drying scale, and wherein said step (b) comprises:

(b1) moving said radiating source relative to said housing to said drying position.

29. The method as claimed in claim 27, wherein said radiating source is at least partially surrounded by a carriage and operably connected to said carriage, wherein said step (b) comprises:

(b1) moving said radiating source to said drying position by moving said carriage to said drying position, and wherein said step (a1) comprises:

(a1a) moving said radiating source to said loading position by moving said carriage to said loading position.

30. The method as claimed in claim 29, wherein said carriage comprises a carriage cover that covers a upper side of said radiating source.

31. The method as claimed in claim 30, wherein said carriage cover covers lateral sides of said radiating source.

32. The method as claimed in claim 29, wherein said carriage comprises a front cover that covers a front portion of said radiating source.

33. The method as claimed in claim 32, wherein said front cover passes completely over said sample when said carriage moves to said drying position, and wherein said front cover contains a viewing notch in a bottom edge of said front cover so that an operator of said drying scale can view said sample through said front cover when said carriage is located in said drying position.

34. The method as claimed in claim 33, wherein a viewing window is operably connected to said carriage and moves between said loading position and said drying position with said carriage, and wherein said step (b1) comprises:

(b1a) lowering said viewing window adjacent to said viewing notch when said carriage is moved to said drying position so that said sample is not substantially exposed via said viewing notch, and wherein said step (a1a) comprises:

(a1a1) raising said viewing window with respect to said front cover when said carriage is moved from said drying position to said loading position.

35. The method as claimed in claim 34, wherein at least a portion of said viewing notch of said front cover is located below a lower edge of said radiating source, and wherein said step (b1a) comprises:

(b1a1) raising said viewing window such that a lower edge of said viewing window is located just below said lower edge of radiating source when said carriage is moved from said drying position to said loading position.

* * * * *

UNITED STATES PATENT AND TRADEMARK OFFICE
CERTIFICATE OF CORRECTION

PATENT NO. : 6,255,603 B1
DATED : July 3, 2001
INVENTOR(S) : Wilfried Spannagel, August Heine, Norbert Winkler It is certified that error appears in the above-identified patent and that said Letters Patent is hereby corrected as shown below:

<u>Title page,</u>
Assignee, "Shartorious AG" should read -- Sartorius AG --

Signed and Sealed this

Fifth Day of February, 2002

Attest:

JAMES E. ROGAN
*Director of the United States Patent and Trademark Office*

*Attesting Officer*